United States Patent [19]

deCastro et al.

[11] Patent Number: 4,999,288

[45] Date of Patent: Mar. 12, 1991

[54] TEST COMPOSITION AND METHOD FOR THE DETERMINATION OF ANILIDES

[75] Inventors: Aurora F. deCastro, Union, Mich.; Surendra K. Gupta, Elkhart; Steven M. Shantz, Goshen, both of Ind.

[73] Assignee: GDS Technology, Inc., Elkhart, Ind.

[21] Appl. No.: 116,169

[22] Filed: Oct. 28, 1987

[51] Int. Cl.$^5$ .................. C12Q 1/34; C12Q 1/28; C12N 9/96

[52] U.S. Cl. ........................ 435/18; 435/28; 435/188; 435/810

[58] Field of Search .................. 435/18, 188, 28, 810; 252/89

[56] References Cited

U.S. PATENT DOCUMENTS

| | | | |
|---|---|---|---|
| 3,557,002 | 11/1967 | McCarty | 252/89 |
| 4,414,327 | 11/1983 | Hammond et al. | 435/18 |
| 4,473,550 | 9/1984 | Rosenbaum et al. | 424/94 |
| 4,668,620 | 5/1987 | Armenta et al. | 435/7 |

*Primary Examiner*—Esther L. Kepplinger
*Assistant Examiner*—Laurie A. Scheiner
*Attorney, Agent, or Firm*—McDermott, Will & Emery

[57] ABSTRACT

A method and unitized test composition is described for the estimation of an anilide in which the enzymatic hydrolysis of the anilide and colorimetric quantitation of aniline or aniline derivative can be done simultaneously.

The hydrolysis of the anilide is catalyzed by a known enzyme, arylacylamidase, E. C. 3.5.1.13. Stabilization of the enzyme is provided by the addition of controlled amounts of a compound containing alcoholic and/or aromatic groups such as ortho-cresol, isopropanol or benzoate.

Basically, the unitized test composition comprises (i) arylacylamidase, (ii) a controlled amount of an organic compound containing alcoholic and/or aromatic groups which acts as both a stabilizer for the arylacylamidase and forms a colored product with aniline, and (iii) a novel oxidant/catalytic agent for accelerating color development.

The benefit of such methodology results in a one step addition of the complete reagent to the sample, serum or matrix containing the anilide as opposed to a several step addition. The consequence of this is that only one reagent channel is required to perform the test in an automated analyzer as opposed to the usual requirement that several channels be utilized. This method also makes possible the development of a solid-phase test device such as a dip and read test strip containing all the reagents necessary for the test of an anilide.

In addition, a method for the stabilization of arylacylamidase enzyme is described.

9 Claims, No Drawings

TEST COMPOSITION AND METHOD FOR THE DETERMINATION OF ANILIDES

BACKGROUND OF THE INVENTION

This invention relates to a method of stabilizing the enzyme arylacylamidase as well as a simplified enzymatic method and composition for the quantitation of anilide compounds, i.e. N-acylated primary aromatic amines or N-substituted acetamides including N-arylacetamides, such as acetaminophen (4-hydroxyacetanilide) in samples containing these drugs including biological fluids such as urine, plasma, serum or blood.

Acetaminophen, for example, is commonly used as an analgesic and antipyretic. It is found in many formulations promoted for the relief of pain, cough and colds. Because it can produce adverse side effects, its quantitation or estimation in cases of overdose is particularly important. Cases of overdose may lead to hepatic necrosis with possible fatal hepatic failure as reported in Ann. of Int. Med., 87, 202 (1977). The plasma concentration of acetaminophen is indicative of clinical evidence of liver damage. In cases of overdose known antidotes are administered. Therefore, the simplest and quickest method of testing for this material provides the greatest advantage to the patient.

Several chemical methods for the estimation of an anilide are known. These methods involve the addition of chemical reagents to the solution containing the anilide and the spectrophotometric determination of the resulting colored compound. Examples of these methods are described by J. H. Routh, et al., Clin. Chem. 14, 882 (1968), S. L. Tompsett, Ann. Clin. Biochem. 6, 81 (1969), J. P. Glynn, et al. Lancet 1, 1147 (1975) and G. S. Wilkinson, Ann.Clin. Biochem. 13, 435 (1976). In some of these methods, after the anilide is chemically hydrolysed by acids under a variety of conditions of temperature and time, the resulting aniline or aniline derivative formed is reacted with a substituted phenol or phenolic ether, such as ortho-cresol to give color which can be spectrophotometrically measured at 615 nm.

It has also been known for many years that several organisms produce enzymes (arylacylamide amidohydrolase or arylacylamidase) defined in group E. C. 3.5.1.13, capable of hydrolysing N-arylacylamides. Examples are R. P. Lanzilotta Ph.D. Thesis, Rutgers University, New Brunswick, N.J. 1968, N. E. Sharabi et al. App. Microb. 18, 369 (1969), D. J. W. Grant et al., Microbio. 8, 15 (1973). J. Alt et al. in J. of Gen. Microb. 87, 260 (1975) also found another bacterial strain of Pseudomonas (gram negative rods) namely *Pseudomonas acidovorans* ATCC 15668 which contains an arylamidase E. C. 3.5.1.13 which also hydrolyses anilides.

Moreover, it has been previously disclosed that the enzymatic hydrolysis of the anilide p-nitroacetanilide to an aniline can be measured spectrophotometrically at 405 nm. The spectrophotometric estimation of the anilide produced by another arylacylamidase enzyme was also reported in U.K. patent GB 2089978 B (1984), U.S. Pat. No. 414,327 (1983) and P. M. Hammond, et al. in Anal. Biochem. 143, 152 (1984). In these publications, hydrolysis of anilides is accomplished by an enzyme. The enzyme E. C. 3.5.1.13 described was derived from a *Pseudomonas species*, namely *Pseudomonas fluorescens* ATCC 39005 and *Pseudomonas putida* ATCC 39004.

The aniline or aniline derivative thus produced was measured spectrophotometrically at 615 nm by a method similar to previously described methodologies using as an oxidizing agent a Cu II salt (or Fe III, chromate, dichromate or permanganate salt), a base in the form of a solution of ammonia and phenol or phenolic ether such as ortho-cresol.

These previous teachings were put to practice by Porton Products in a kit for the determination of acetaminophen in serum which comprises the sequential addition to serum of first an enzyme reagent followed by incubation for three minutes, a second addition of reagent A (1% ortho cresol solution) and a third addition of reagent B (ammoniacal copper solution). The color produced is read spectrophotometrically at 615 nm.

However, there are two problems associated with this methodology, (1) the three step addition of reagents makes the procedure cumbersome if done as a manual method and (2) the method cannot be conveniently automated in most instruments as it would require using three separate reagent channels to do one test plus a preincubation step prior to the addition of the two final reagents.

Accordingly, the present invention provides a simplified methodology for the determination of anilides by providing (a) a stabilized arylacylamidase enzyme preparation which can be conveniently integrated into a stable reagent to be used in any method for the determination of an anilide (b) a composition of reagents which can be made into one reagent so that the serum or matrix containing the drug can be added to it and measured spectrophotometrically in a one step reaction (c) by providing a format, as one reagent, which can be easily used with automated instruments by occupying only one channel as opposed to three channels and, (d) a stable composition of reagents that can be made into a solid-phase reagent test device.

DESCRIPTION OF THE PREFERRED EMBODIMENTS

The principle of the method of the present invention is based on the enzymatic convertion of anilide to aniline or aniline derivative by an arylacylamidase enzyme. In the case of acetaminophen, it converts the anilide, to 4-hydroxyaniline. The 4-hydroxyaniline can then react with a phenol derivative, such as ortho-cresol, to produce color. This can be shown by the following equations:

Acetaminophen 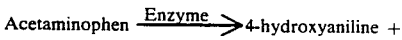 4-hydroxyaniline + phenol derivative  Colored Product

Because the second reaction described above is relatively slow using the prior art methods, catalyst/oxidants must be used to accelerate the color forming reaction. However, conditions and means previously described in publications to accelerate this reaction tend to inhibit the enzyme reaction. A novel catalyst/oxidant is provided in the present invention to allow all reactions to proceed simultaneously. It has also been unexpectedly found that the present combination of reagents can be accomplished because of the addition or use of a much milder calalyst/oxidant, such as periodate, to the stabilized enzyme and phenolic derivative mixture instead of the ammonium hydroxide or ammoniated copper solution previously disclosed. The addition of such prior art catalyst/oxidants inhibits the enzyme reaction from taking place, thus requiring the previously noted sample/enzyme incubation prior to the addition of reagents. By substituting milder oxidants such as periodates, tho enzymatic reaction, as well as the color formation can take place in a one step procedure.

The arylacylamidase enzyme E. C. 3.5.1.13 used in the present invention was obtained from GDS TECHNOLOGY, INC., Elkhart, Ind. It was isolated from a Gram positive organism other than *Pseudomonas sp.* and was obtained in a lyophylized form free from glycerol.

The arylacylamidase enzyme hydrolyses the amide bond at pH's between 6.5 and 9.5 converting an anilide like acetaminophen to 4-hydroxyaniline. Preferred buffers are borates and carbonates. It has also been found that the addition of controlled amounts of certain substances containing alcoholic and/or aromatic groups such as, for example, isopropanol, sodium benzoate and ortho-cresol provide the required stabilization of the enzyme. This stabilization of acrylacylamidase is very critical because it allows the preparation of a stable reagent composition in liquid or solid phase format including electrochemical methods which can be used for the determination of anilides.

It is also necessary that a controlled amount of stabilizer be used in the compositions of the present invention. For example it was found that 10-100 mg/100 ml of ortho-cresol enhances the enzyme stability. This is in contrast to previously used higher concentrations of ortho-cresol (about 1%) as described in U.K. Patents 2089978 and 4414327. Such high concentrations tend to inactivate the enzyme and make it unstable.

Importantly and unexpectedly, it has also been found that the same amount of ortho-cresol necessary for the stabilization of the enzyme is sufficient to allow the color reaction to take place simultaneously with the enzymatic reaction. Phenol and other phenol derivatives such as guaiacol can be used to produce color with 4-hydroxyaniline, but at a slower rate. It has been further found that the addition of an oxidizing agent, like periodate, in small amounts considerably speeds up the reaction of the aniline and the phenolic derivative producing color faster. This catalytic agent is also stable at a wide range of pH. Other chemicals like persulfate or hydrogen peroxide and peroxidase also catalyze the color producing reaction.

It has also been found that certain compounds will stabilize the arylacylamidase but do not develop color in the presence of an aniline. Such compounds are sodium benzoate and isopropanol. In such instances color producing compounds such as ortho-cresol or phenol derivatives must be included in the test reagent composition.

EXAMPLES

Example 1

Example 1 illustrates the stabilizing effect of some of the above mentioned agents on the enzyme.

Arylacylamidase enzyme was dissolved in a 50 mM Borate buffer at various pH's at widely different concentrations of between 1 and 1500 U/L in the presence of between about 1 and 12 mM ortho-cresol. An equivalent solution of enzyme in buffer was prepared in the absence of ortho-cresol. Both solutions were placed at 37 degrees C. for a period of two weeks. The enzyme activity was measured at the beginning as well as at certain times during the two week period. The enzyme activity was determined by a method which uses Tris-HCl pH 8.5 and paranitroacetanilide as the enzyme substrate. The kinetic assay was performed at 30 degrees C. and 405 nm.

Table 1 illustrates this stability of the enzyme in presence of ortho-cresol.

TABLE 1

REMAINING ENZYME ACTIVITY IN U/ml At 37 DEGREES C.

| CONDITION | 0 | 5 hrs. | 3 days | 7 days | 14 days |
|---|---|---|---|---|---|
| pH 8.0, No o-cresol | 13.5 | 12.9 | 9.44 | 4.71 | 1.87 |
| pH 8.0, 2.8 mM o-cresol | 13.6 | 13.5 | 13.6 | 12.3 | 11.8 |
| pH 8.0, No o-cresol | 6.26 | 5.81 | 4.15 | 2.01 | 0.85 |
| pH 8.0, 4.2 mM o-cresol | 6.25 | 6.16 | 6.20 | 5.66 | 5.36 |
| pH 9.0, No o-cresol | 13.6 | 5.09 | 0.06 | 0 | 0 |
| pH 9.0, 2.2 mM o-cresol | 13.6 | 13.7 | 11.2 | 9.26 | 5.44 |
| pH 9.0, No o-cresol | 6.16 | 2.27 | 0 | 0 | 0 |
| pH 9.0, 3.75 mM o-cresol | 6.15 | 6.20 | 5.03 | 4.16 | 2.36 |

At all enzyme concentrations and all pH's, the remaining enzyme activity was much higher when ortho-cresol was present than when it was absent. Higher remaining activity resulted when the test was conducted at room temperature and at 4 degrees C. instead of at 37 degrees C. Similar results were obtained when isopropanol and benzoate were added to arylacylamidase enzyme preparations at concentrations of about 0.1 to 12% in the case of isopropanol and of about 1 to 15 mg/ml in the case of benzoate.

Different concentrations of aryaclyamidase enzyme were dissolved in buffer at pH's of from 7.0 to 9.5 in the presence of about between 1 to 12 mM ortho-cresol. This reagent alone produced color with time when serum containing p-hydroxyaniline was added to it. When guaiacol or phenol were substituted for the ortho-cresol, the development of color was even slower. Solutions of an oxidizing agent such as periodate at concentrations of about 1 to 15 mM enhances the speed of the color reaction as did persulfate and a combination of hydrogen peroxide and peroxidase. Periodate was however preferred. Some of the combinations used and the results obtained are shown in examples 2 to 4.

Sodium benzoate was also used to stabilize the enzyme for use in a liquid assay as well as in an electrochemical assay.

Example 2

Arylacylamidase enzyme at a concentrations of 3.5 U/L was dissolved in 25 mM Borate buffer at pH 8.0 containing 3.75 mM ortho-cresol. A solution of 3.75 mM periodate in 50 mM Borate buffer at pH 9.3 was also prepared. The two solutions were mixed at a ratio of 2 parts of enzyme/ortho-cresol solution to 1 part periodate solution to make the final reagent. To 2 ml of the above reagent mixture 50 ul of serum containing various concentrations of acetaminophen was added. The rate of color produced at 37 degrees C. was read at 615 nm. Table 2 shows the absorbance rate per minute as a function of concentration.

TABLE 2

| Concentration of p-hydroxyacetanilide in serum in mg/L | OD/min |
|---|---|
| 50 | 0.0093 |

TABLE 2-continued

| Concentration of p-hydroxyacetanilide in serum in mg/L | OD/min |
|---|---|
| 100 | 0.0186 |
| 200 | 0.0411 |
| 400 | 0.0807 |

The absorbance rate shows a linear relationship with the acetaminophen concentration. Similar but lower readings were obtained when similar concentrations of guiacol or phenol were substituted for the ortho-cresol.

Instead of periodate, persulfate and hydrogen peroxide and peroxidase were also used to enhance the speed of the color reaction with similar rates of absorbance. The peroxidase system showed catalytic affects at about 0.14 mM $H_2O_2$ and 0.3 U/ml of peroxidase

Example 3

Arylacylamidase enzyme at a concentrations of 5 U/L was dissolved in 50 mM Borate buffer at pHs 8.0 and 9.0 containing 4.5 mM ortho-cresol. Solutions of 5 mM periodate in 50 mM Borate buffer at pH's 9.5 and 11.0 were also prepared. The enzyme/ortho-cresol solution and the periodate solution were mixed at a ratio of 2 to 1 respectively. To 2 ml of each the above reagent mixtures 50 ul or 100 ul of serum containing various acetaminophen concentrations was added. The rate of color produced at 37 degrees C. was read at 615 nm. Table 3 shows the absorbance rate per minute as a function of concentration in both cases:

TABLE 3

| Concentration of p-hydroxyacetanilide in serum in mg/L | Enzyme solution at pH 8.0 50 ul serum OD/min | Enzyme solution at pH 9.0 100 ul serum OD/min |
|---|---|---|
| 50 | 0.0111 | 0.0177 |
| 100 | 0.0221 | 0.0370 |
| 200 | 0.0422 | 0.0702 |
| 400 | 0.0807 | 0.1390 |

In each case the OD/min shows a linear relationship with the acetaminophen concentrations. Similar but lower readings were obtained when similar concentrations of guiacol or phenol were substituted for the ortho-cresol.

Example 4

Arylacylamidase enzyme at a concentrations of 3.5 U/L was dissolved in 50 mM carbonate buffer at pH 8.0 containing 3.75 mM ortho-cresol. A solution of 3.75 mM periodate in 50 mM carbonate buffer at pH 9.6 was also prepared. The two solutions were mixed at a ratio of 2 to 1 respectively. To 2 ml of the combined reagent mixture 50 ul of serum containing various acetaminophen concentrations was added. The rate of color produced at 37 degrees C. was read at 615 nm. Table 4 shows the absorbance rate per minute as a function of concentration.

TABLE 4

| Concentration of p-hydroxyacetanilide in serum in mg/L | OD/min |
|---|---|
| 50 | 0.0499 |
| 100 | 0.0885 |
| 200 | 0.1620 |

TABLE 4-continued

| Concentration of p-hydroxyacetanilide in serum in mg/L | OD/min |
|---|---|
| 400 | 0.2940 |

Using carbonate buffer there was also a linear relationship with the rate of color formation and the acetaminophen concentration. Similar but lower readings were obtained when similar concentrations of guiacol or phenol were substituted for the ortho-cresol.

Example 5

Ten by ten mm squares of filter paper were impregnated with a solution containing arylacylamidase enzyme of various concentrations. For example, 100 U of enzyme per ml of borate buffer, pH 9.0. This solution also contained 10 mM ortho-cresol. The paper was air dried and dipped into a solution containing 15 mM sodium periodate. When 50 ul serum containing different concentrations of acetaminophen was added to these paper strips increasingly deeper shades of blue appeared corresponding to increasing acetaminophen concentrations. The gradation of blue color allowed the estimation of the different acetaminophen concentrations.

Example 6

Different concentrations of peroxidase and hydrogen peroxide were added to 2 ml of 50 mM Borate buffer pH 9.0 containing about 3.5 U arylacylamidase and about 2.5 mM ortho-cresol. Fifty microliters of serum containing different amounts of acetaminophen were then added. The color of the solution produced at 37 degrees C. was read at 615 nm. Table 5 shows the rate of color development when 10 U of peroxidase and 50 ul of 0.025% $H_2O_2$ was added.

| Concentration of p-hydroxyacetanilide in serum in mg/L | OD/min |
|---|---|
| 50 | 0.018 |
| 100 | 0.038 |
| 200 | 0.079 |

What is claimed is:

1. A test composition for detecting anilides comprising an arylacylamidase enzyme E. C. 3.5.1.13, a compound containing aromatic groups which is capable of developing a colored compound in the presence of aniline or an aniline derivative and an oxidant/catalyst selected from the group consisting of periodate persulfate and peroxidase compounds in an amount sufficient for accelerating development of said color compound.

2. A test composition as in claim 1 wherein the compound containing aromatic groups is selected from the group consisting of ortho-cresol, phenol and guaiacol.

3. A test composition as in claim 1 which additionally contains a buffer for maintaining the pH of the composition in a range of from about 7.0 to about 9.5.

4. A test composition as in claim 3 wherein the buffer is selected from the group consisting of borates and carbonates.

5. A method for the determination of an anilide in an aqueous fluid comprising contacting the fluid with a unitized reagent composition consisting of arylacylamidase enzyme E.C. 3.5.1.13, a compound containing aromatic groups which develops color in the presence of aniline or an aniline derivative and an oxidant/catalyst selected from the group consisting of periodate, persulfate and peroxidase compounds in an amount sufficient for allowing the resulting color to develop and correlating the amount of color developed to the concentration of anilide in the fluid.

6. A method as in claim 5 wherein the reagent composition additionally contains a buffer for maintaining the fluid at a pH of about 7.0 to about 9.5.

7. A method as in claim 5 wherein the compound containing aromatic groups is selected from the group consisting of ortho-cresol, phenol and quaiacol.

8. A test device for detecting anilides comprising a solid state matrix impregnated with a test composition consisting of arylacylamidase enzyme E.C. 3.5.1.13, a compound containing aromatic groups which develops color in the presence of aniline and an oxidant/catalyst selected from the group consisting of periodate, persulfate and peroxidase compounds in an amount sufficient for accelerating development of said color.

9. A test device as in claim 8 wherein the compound containing aromatic groups is selected from the group consisting of ortho-cresol, phenol and quaiacol.

* * * * *